United States Patent [19]

Fleischhacker, Jr.

[11] Patent Number: 5,984,877
[45] Date of Patent: Nov. 16, 1999

[54] GUIDE WIRE MARKER TECHNIQUE AND COIL SPRING MARKER TECHNIQUE

[76] Inventor: Joseph F. Fleischhacker, Jr., 5601 Bartlett Blvd., Mount, Minn. 55364

[21] Appl. No.: 07/651,326

[22] Filed: Feb. 5, 1991

[51] Int. Cl.⁶ ........................................................ A61B 5/00
[52] U.S. Cl. ............................................................. 600/585
[58] Field of Search .................................... 128/657, 772; 604/95, 170; 600/585

[56] References Cited

U.S. PATENT DOCUMENTS

| | | | |
|---|---|---|---|
| 4,215,703 | 8/1980 | Willson | 128/772 |
| 4,538,622 | 9/1985 | Samson et al. | 128/657 |
| 4,554,929 | 11/1985 | Samson et al. | 128/772 |
| 4,719,924 | 1/1988 | Crittenden et al. | 128/772 |
| 4,748,986 | 6/1988 | Morrison et al. | 128/772 |
| 4,763,647 | 8/1988 | Gambale | 128/657 |
| 4,922,924 | 5/1990 | Gambale et al. | 128/772 |
| 4,932,419 | 6/1990 | de Toledo | 128/772 |
| 5,174,302 | 12/1992 | Palmer | 128/772 |

*Primary Examiner*—Max Hindenburg
*Attorney, Agent, or Firm*—Michael Best & Friedrich LLP; Grady J. Frenchick

[57] ABSTRACT

An apparatus and method of providing radiopaque marking for a coil spring. The coil spring will typically be used for medical applications within the cardiovascular system or other region wherein the assistance of a spring guide wire is necessary or desirable. Likely applications may include guide wires, angioplasty catheters, or infusion catheters. The basic spring guide wire is formed of a multifilar (e.g. quadrifilar) structure. At least one of the wires within the quadrifilar structure is drawn from a highly radiopaque material, such as platinum or a platinum alloy. The remaining wires are of a convenient base material such as stainless steel. The resulting quadrifilar structure will provide a degree of radiopacity over its length with one of four strands being highly visible under fluoroscopic energy. Various points along the spring guide wire may be further distinctively marked by changing the number of strands within the multifilar structure. One platinum wire within a trifilar structure is more visible fluoroscopically than in a quadrifilar structure. Similarly, the single platinum wire becomes correspondingly even more visible in bifilar and unifilar structures. These transitions are easily implemented in the coil winding process through the simple termination of one or more of the wires of the base material with a corresponding change in winding pitch of the remaining wire(s). The result is a marking of various points along the spring guide wire without the addition of any stiffness or change in handling characteristics.

23 Claims, 9 Drawing Sheets

GUIDE WIRE MARKER TECHNIQUE AND COIL SPRING MARKER TECHNIQUE

CROSS REFERENCE TO CO-PENDING APPLICATIONS

None.

BACKGROUND OF THE INVENTION

1. Field of the Invention

The present invention generally relates to medical devices, and more particularly, relates to guide wires and coils with radiopaque markings. Specifically, the present invention pertains to a radiopaque wire in a guide wire to provide visibility of the guide wire.

2. Description of the Prior Art

The desirability of using coils of wire for spring guide wires to provide structural integrity for and improve the handling characteristics of guide wires and catheters is known. Usually these devices are designed to traverse a finite distance within the body of the patient and within the vascular system, urethra, or other passageway of the patient.

The coil spring may run the entire length of the medical device or be appended in a particular region, such as the distal end.

Most spring guide wires are wound as single filar coils. U.S. patent application Ser. No. 07/384,398, filed on Jul. 24, 1989, entitled "Hollow Lumen Cable Apparatus" by Fleischhacker et al., describes multifilar spring guide wires. While the multifilar spring guide wires may be more expensive to implement, the multifilar spring guide wires are perceived to have superior handling characteristics.

It is very desirable to mark positions along the length of the device to more accurately position the device within the patient's body under fluoroscopy. This is usually accomplished through the use of a platinum or platinum alloy coil.

U.S. Pat. No. 4,538,622 issued to Samson et al., and U.S. Pat. No. 4,545,390 issued to Leary each employ a separate coil of a radiopaque material. However, placement of a marker using these approaches tends to undesirably add to cost, either in the form of excessive use of the platinum alloy and/or the necessary addition of tedious assembly steps.

In some cases, it may be advantageous to visualize the entire coil length of a guide wire under fluoroscopy so as to see the guide wire track in the vasculature. It may also be desirable to mark just the distal tip section of the guide wire or other predetermined points of the guide wire as deemed necessary.

The prior art devices do not provide a solution to both problems. If a guide wire is designed with a coil which is entirely radiopaque, one cannot easily see other device markers passing over it, but the guide wire coil can be easily seen over its entire length.

The present invention overcomes the disadvantages of the prior art spring guide wires by providing a technique for radiopaque marking which is both flexible and easily implemented while at the same time having minimum or negligible impact on the handling characteristics of the resulting device. The device can be manufactured to provide a soft trace of radiopacity in the main body of the coil so it can be visualize yet not obscure other markers riding over it, and in the same coil provide a pronounced radiopaque tip for accurate placement.

SUMMARY OF THE INVENTION

The general purpose of the present invention is to provide a technique for radiopaque marking which is both flexible and easily implemented while at the same time having minimum or negligible impact on the handling characteristics of the resulting device. The device can be manufactured to provide a soft trace of radiopacity in the main body of the coil so it can be visualized and yet not obscure other markers riding over it, and in the same coil provide a more pronounced radiopaque tip for accurate placement of the tip of the device.

The spring guide wire is wound as a multifilar structure consists of a plurality of wires, preferably four wires. At least one of the wires consists of a highly radiopaque material, such as platinum or a platinum alloy. The resulting spring guide wire shows under fluoroscopy as a relatively faint, but viewable perceptible trace along the length of the guide wire.

Various points along the coil of the spring guide wire can be delineated by changing the number of separate strands of wire within the coil structure or guide wire structure. If a decreasing filar coil with one platinum wire reverts to a trifilar coil with the same one platinum wire, a more pronounced trace will be visible. The trace will become yet more pronounced as a bifilar and then as unifilar spring guide wire while retaining the platinum wire.

Changes in the coil structure are easily implemented in the winding process by terminating one or more strands short of the distal end of the spring guide wire. To accommodate the change, the remaining wire(s) must be wound with a decreased pitch to maintain the same winding space (e.g., close wound), and may also be open pitch as well to enhance flexibility of the distal tip.

Because the basic structure of the spring guide wire is maintained from proximal to distal end without the addition of other elements (e.g., a separate marker coil), the handling characteristics are not compromised by the addition of separate component structures and tend to be consistent. Because the marker(s) are fabricated during the coil winding process, the resultant structure is integral and is made up of multiple components, such as four wires by way of example and for purposes of illustration only, and not to be construed as limiting as any suitable number of filars can be utilized.

A more abrupt change can be accomplished by changing the coil spring from one platinum wire in a quadrifilar structure to a monofilar platinum coil by terminating all of the base metal strands at one point. This results in a faint viewable trace under radioscopic visualization throughout most of the coil length to a very visible distal segment. More than one strand of platinum wire may be used in the main body of the guide wire for additional visualization. A quadrifilar coil can also be utilized for improved torque response.

According to one embodiment of the present invention, there is provided a PTCA wire with platinum tracer and integral distal spring. The design provides radiographic visualization throughout the coil length, but without the potential for poor visualization by providing a tracer wire in the proximal area of the spring for subdued visualization. The distal area of the tracer coil can have a decrease in pitch in order to improve or enhance radiographic visualization so as to readily identify the guide wire tip position. The main body of coil is wound with multiple filars incorporating a tracer strand of platinum alloy and can be more than one strand depending on the amount of radiopacity desired. The remaining strands can be stainless steel. Near the distal end, the other filars can drop off, but the platinum radiopaque strand continues to the distal connection. The pitch of distal segments can be varied from tight wound to a space wound between windings to improve flexibility.

Other embodiments are within the teachings and the scope of the present invention, and are particularly applicable in the medical area of guide wires and medical coils in general. The wires or strands of the coil can be round, square, rectangular or any other geometrical cross section.

One significant aspect and feature of the present invention is to provide a method and apparatus for radiopaque marking a coil of wire and particularly a guide wire at predetermined distinct points at various levels of intensity.

Other significant aspects and features of the present invention is to provide a process for marking predetermined points and/or length of a guide wire or a coiled wire. Having thus described principal embodiments of the present invention, it is a principal object hereof to provide a method and system for marking predetermined points of a coil of wire, and particularly a guide wire.

One object of the present invention is to provide a radiopaque wire wound about other wires to provide a predetermined degree of visibility under a fluoroscopic procedure.

Another object of the present invention is to provide a radiopaque marker(s) for predetermined points for a guide wire.

A further object of the present invention is to provide the teachings of the present invention which extend to a flat wire coil for a guide wire, as well as a round wire coil for a guide wire.

An additional object of the present invention is using a tracer or tracer strand of a round or flat wire to indicate the degree of visibility of a guide wire or a particular point of visibility of the guide wire. The degree of radiopacity is determined by either the closeness of the windings or the width or cross section of the radiopaque material at a particular point.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
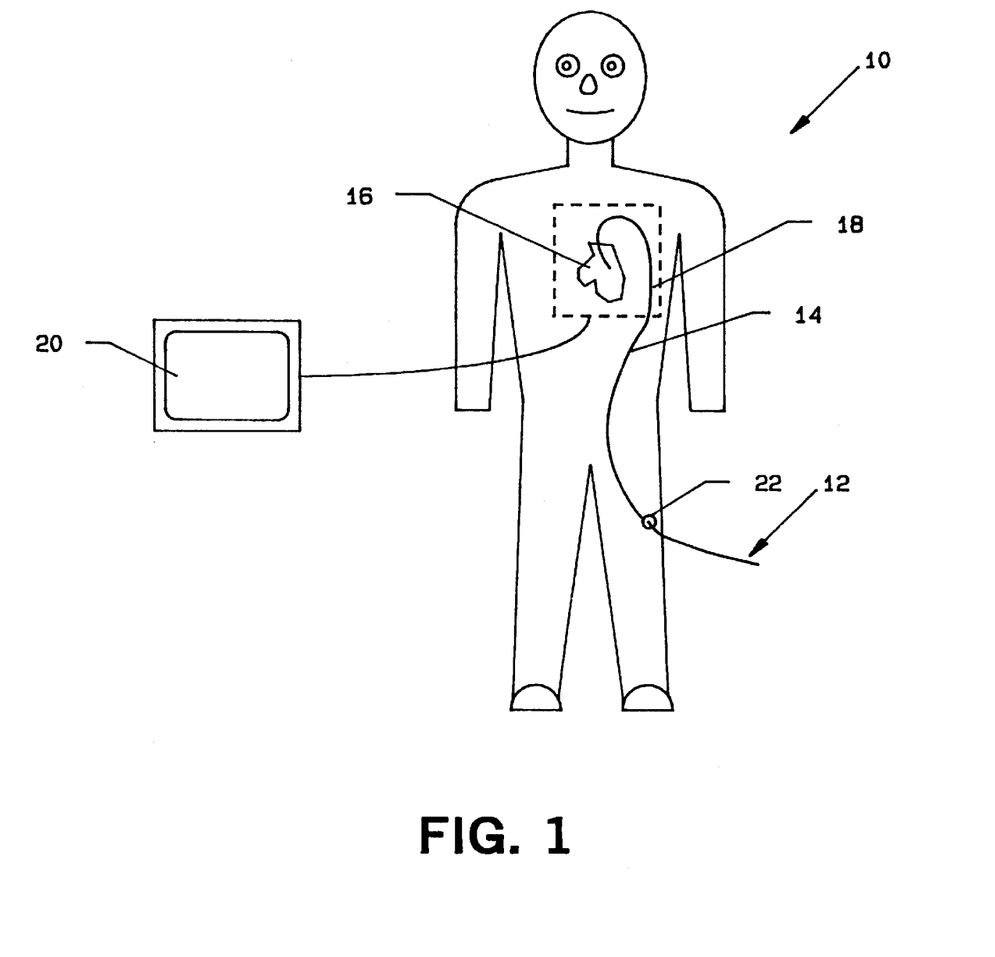
FIG. 1 is a conceptual plan view of the spring guide wire of the present invention as used within a medical procedure.

FIG. 1 is a conceptual plan view of a spring guide wire as employed in a a typical medical procedure. Patient 10 is to be catheterized from entry point 22 of the left femoral artery. Guide wire 12, comprising a spring guide wire (not shown), is inserted at entry point 22 and advanced toward heart 16 through artery 14 of the cardiovascular system.

Attending medical personnel observe the advancement of guide wire 12 on fluoroscopic monitor 20 using a fluoroscopic sensor system head 18. Radiopaque markers (not shown), usually are near the distal end of guide wire 12, which greatly assist the medical personnel in identifying the location of the guide wire 12 in the artery 14 and in the heart 16.

Figure 2:
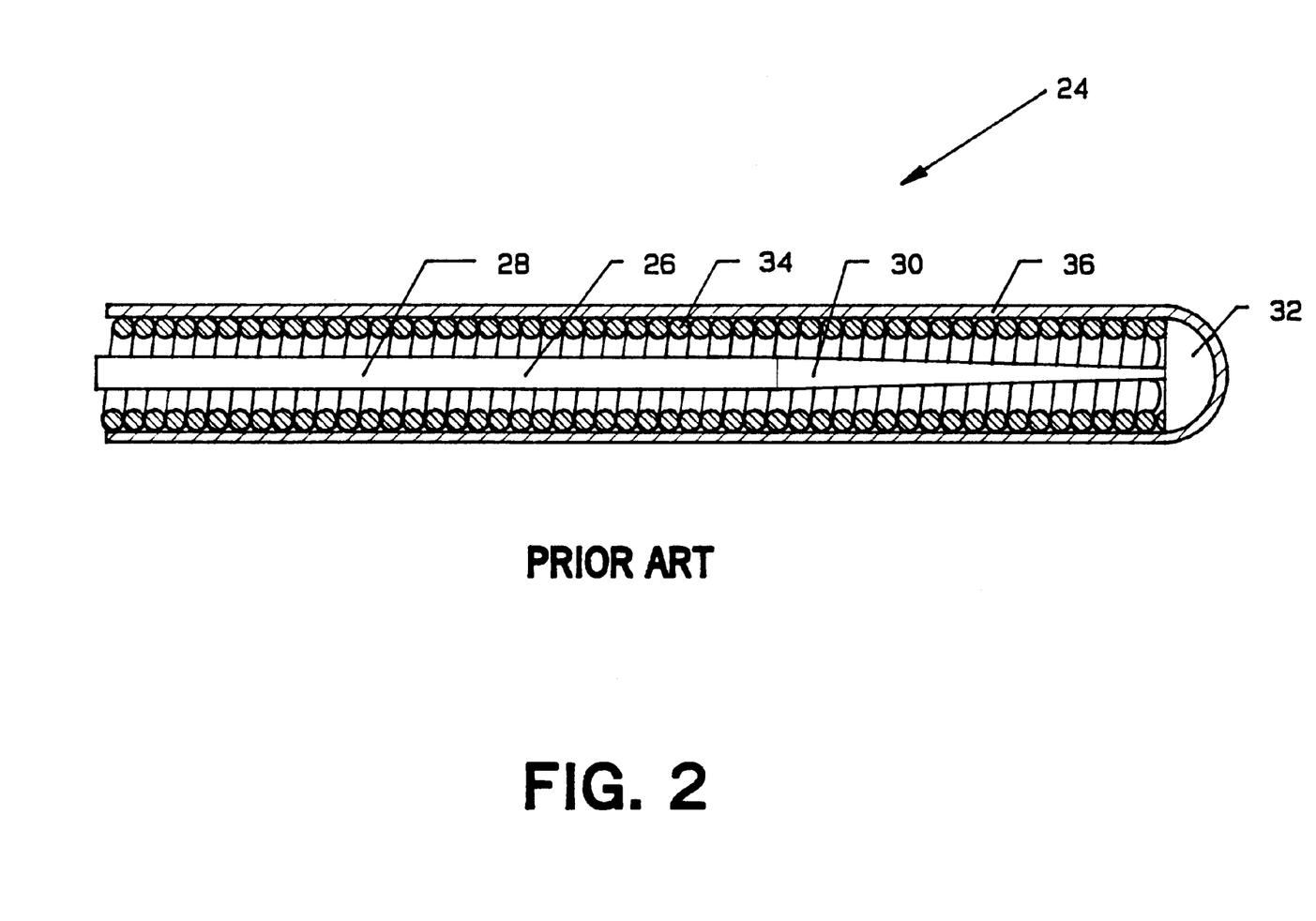
FIG. 2 is a cross-sectional view of a prior art wire.

FIG. 2 is a cross-sectional view of the major components of a prior art wire 24. Along a major length of the wire 24 is a core wire 26 which has a first relatively large diameter cross section 28. To facilitate control of the distal end, core wire 26 is of a tapered cross section 30 and tapers toward the distal tip 32.

The core wire 26 is placed within the central lumen of spring coil 34. Typically, spring coil 34 is a unifilar coil of stainless steel wire. It is attached at the proximal and distal ends to core wire 26 by welding or brazing, thereby forming a spherical distal tip 32.

A continuous coating 36, such as a flexible polymer, is applied over the outer periphery of the spring coil 34, as well as over the distal tip 32.

Figure 3:
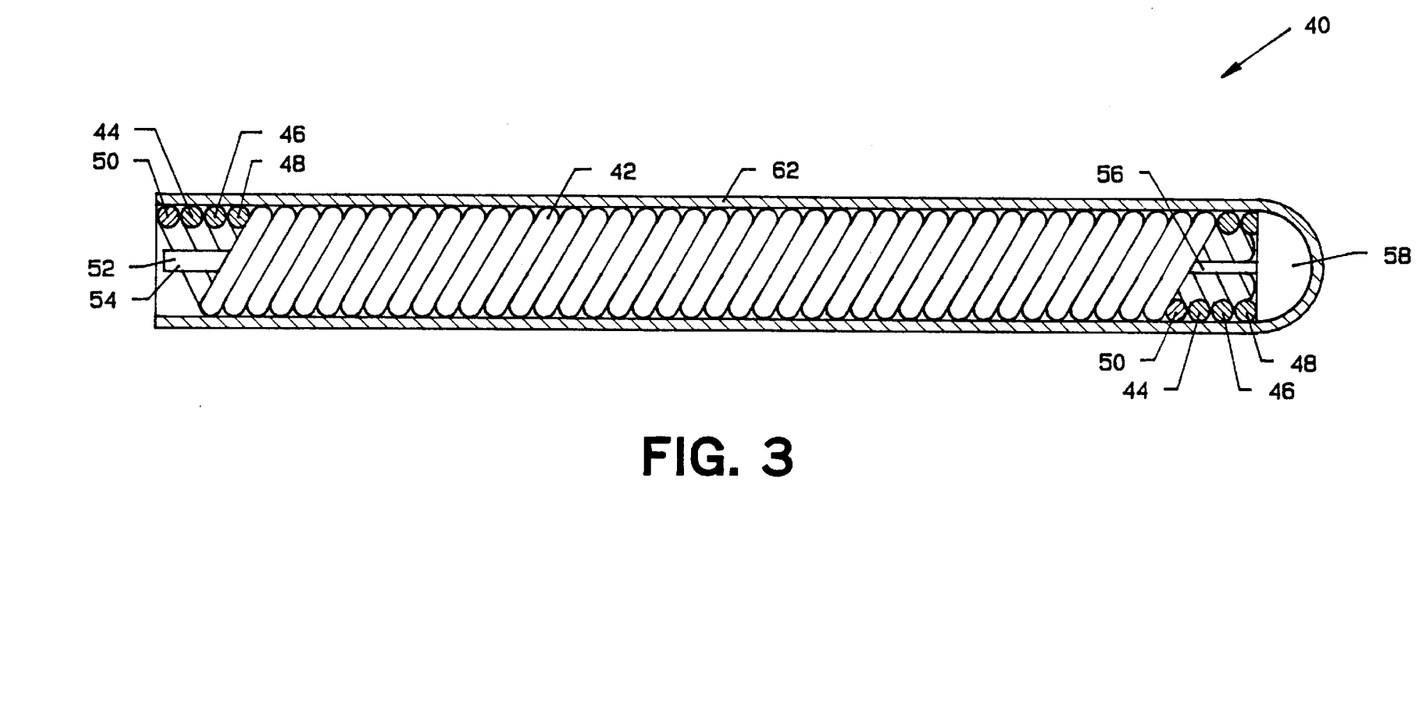
FIG. 3 is a cross-sectional view of a guide wire employing a quadrifilar spring coil.

FIG. 3 is a cross-sectional view of a guide wire 40 employing a quadrifilar spring coil 42. Wire strands 44, 46, and 48 are conveniently drawn from a typical material such as stainless steel. Wire strand 50 is radiopaque in that it is drawn from a radiopaque material, such as a platinum/irridium alloy, and is cross-hatched at a different angle for purposes of illustration.

Along the major length of a guide wire 40, core wire 52 has a first relatively large diameter cross section 54 to facilitate control of the distal end. Core wire 52 is of a decreasing cross section 56 and tapers toward the distal tip 58. The core wire 52 is similar to that core wire 26 as illustrated in prior art discussions of FIG. 2.

The core wire 52 is placed within the central lumen of quadrifilar spring coil 42. Typically, spring coil 42 is a quadrifilar coil of stainless steel wire. It is attached at the proximal and distal ends to core wire 52 by welding, thereby forming a spherical distal tip 58.

A continuous coating 62, such as a flexible polymer, is applied over the outer periphery of the quadrifilar spring coil 42, as well as over the distal tip 58.

The platinum wire strand 50 renders the entire length of the resulting guide wire 40 radiopaque. However, because only one out of four wire strands is radiopaque, the trace/radiopacity is relatively faint for that portion of the spring coil 42 which is quadrifilar by way of example and for purposes of illustration only, and is not to be construed as limiting of the present invention. The teachings of this FIG. can also be expanded to only predetermined portions of the quadrifilar spring coil 42.

Figure 4:
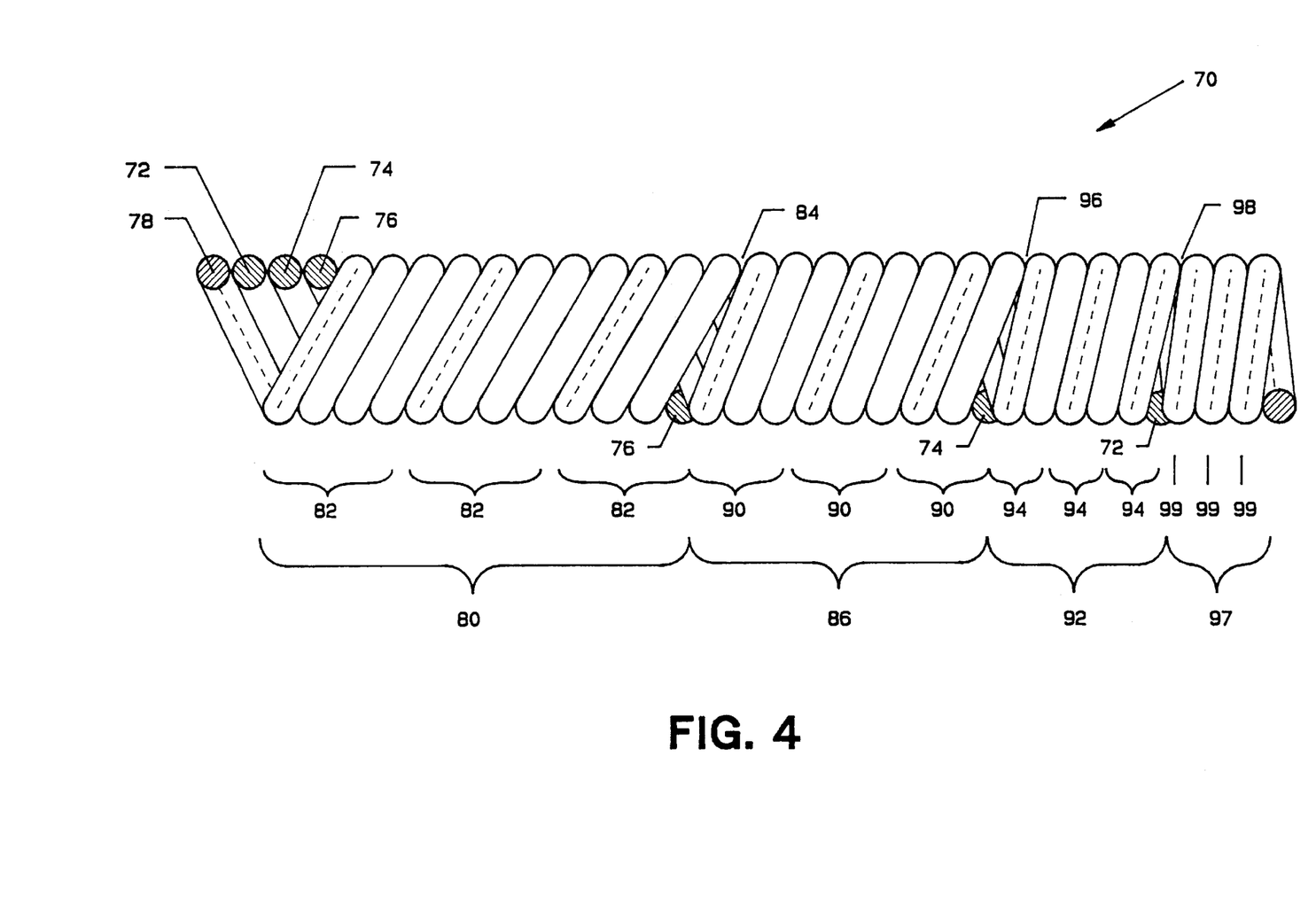
FIG. 4 is an enlarged view of the distal end of a decreasing filar spring coil for a guide wire.

FIG. 4 is an enlarged view of the distal end of decreasing filar spring coil 70. The proximal end of the decreasing filar spring coil 70 is similar to the quadrifilar spring coil 42 of FIG. 3, and includes wire strands 72, 74 and 76 flanked by a radiopaque strand 78, which is crosshatched at a different angle for purposes of illustration. For purposes of illustration, the radiopaque strand 78 is also illustrated with a resident dashed line. The decreasing filar spring coil 70 is quadrifilarly wound over region 80 producing the relatively faint fluoroscopy trace explained above in FIG. 3. Subregions 82 delineate quadrifilar winding groups of four wires. At point 84, however, wire strand 76 is terminated either with or without a substantially smooth taper. The resulting region 86 of the decreasing filar spring coil 70 is trifilar, as depicted by subregion 90 of trifilar groups of three wires, with a correspondingly sharper fluoroscopic trace. The pitch of wire strands 72, 74, and 76 is also decreased within region 86 to maintain the close winding of the decreasing filar spring coil 70.

Region 92 has an even sharper radiopaque trace, as it is bifilar, making platinum wire strand 78 one half of the outer surface area of quadrifilar spring coil 70. The bifilar portion is depicted by subregion 94 and includes groups of two wires. Wire strand 74 is terminated at point 96 with or without a substantially smooth taper, and a corresponding decrease in the pitch of remaining wire strands 78 and 72 in the subregion 94.

The decreasing filar spring coil 70 is unifilar over region 97 having the platinum wire strand 78 as the only wire in the coil. Wire strand 72 is terminated at point 98 with or without a substantially smooth taper. Subregion 99 delineates the unifilar winding of one wire. The fluoroscopic trace of decreasing filar spring coil 70 over region 97 is of a maximum sharpness and also depicts a predetermined condition such as the end of the wire coil.

This manner of constructing the decreasing filar spring coil 70 is by way of illustration only, and is not intended to limit the present invention. Other embodiments using different numbers of wire strands and one or more points of termination can be similarly configured, and are within the teachings and scope of the present invention.

Figure 5:
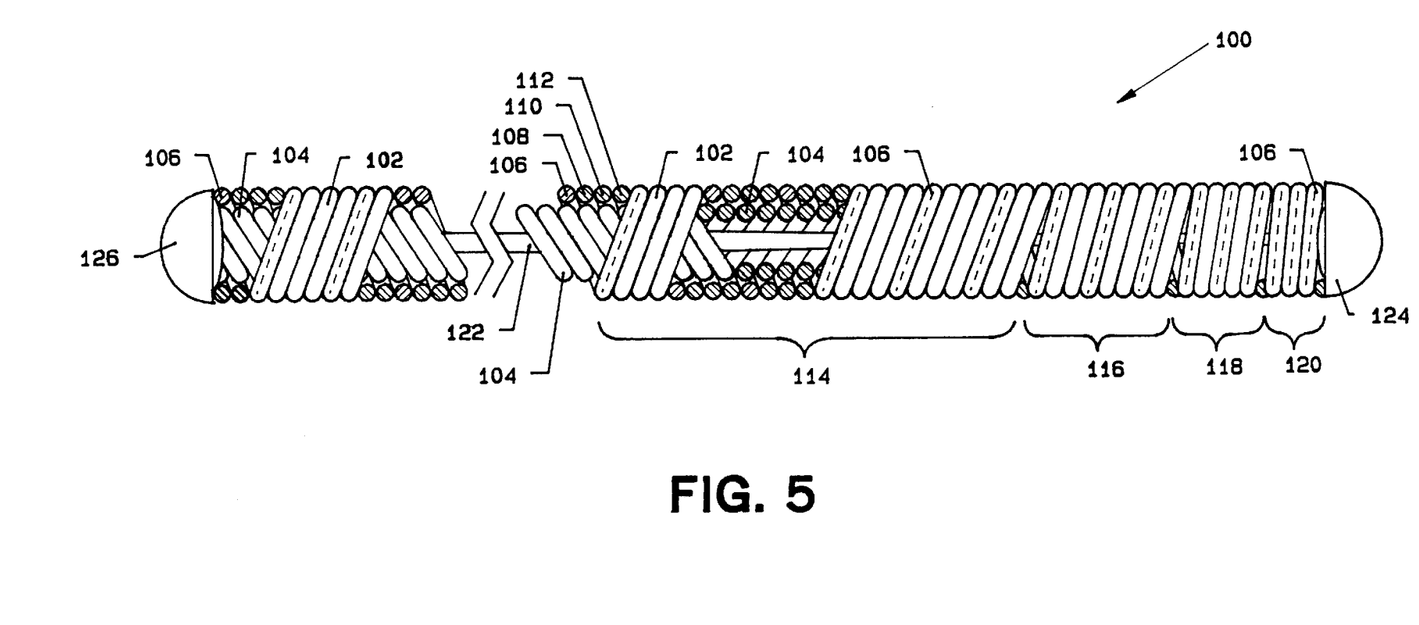
FIG. 5 is a cross-sectioned view of a decreasing filar guide wire.

FIG. 5 is a cross sectional view of a decreasing filar spring coil 102 as utilized in a concentrically wound guide wire 100 incorporating a concentric, and oppositely wound multifilar spring coil 104. The decreasing filar spring coil 102 is the outer coil providing the radiopaque marking, and is similar to the decreasing filar spring coil 70 illustrated in FIG. 4. The decreasing filar spring coil 102 includes a proximal end having a plurality of multifilar wound wires which includes a radiopaque wire strand 106 and adjacent wire strands 108, 110 and 112 wound in a quadrifilar fashion with region 114 including quadrifilar spring windings, region 116 including trifilar spring windings, region 118 including bifilar spring windings, and region 120 of unifilar windings. The radiopaque strand 106 includes a resident dashed line for purposes of illustration only. Multifilar inner spring coil 104 is a quadrifilar coil of conventional construction, although the windings can be less than quadrifilar and decreased with a tracer wire to even further enhance visibility. The tapered core wire 122 is similar to core wire 26 of FIG. 2. The tapered core wire 122, the decreasing filar spring coil 102 and multi filar spring coil 104 are fixedly attached at distal tip 124 and proximal tip 126 by welding or any other suitable securing means such as brazing, electron beam welding, laser welding, or other suitable affixation.

Figure 6:
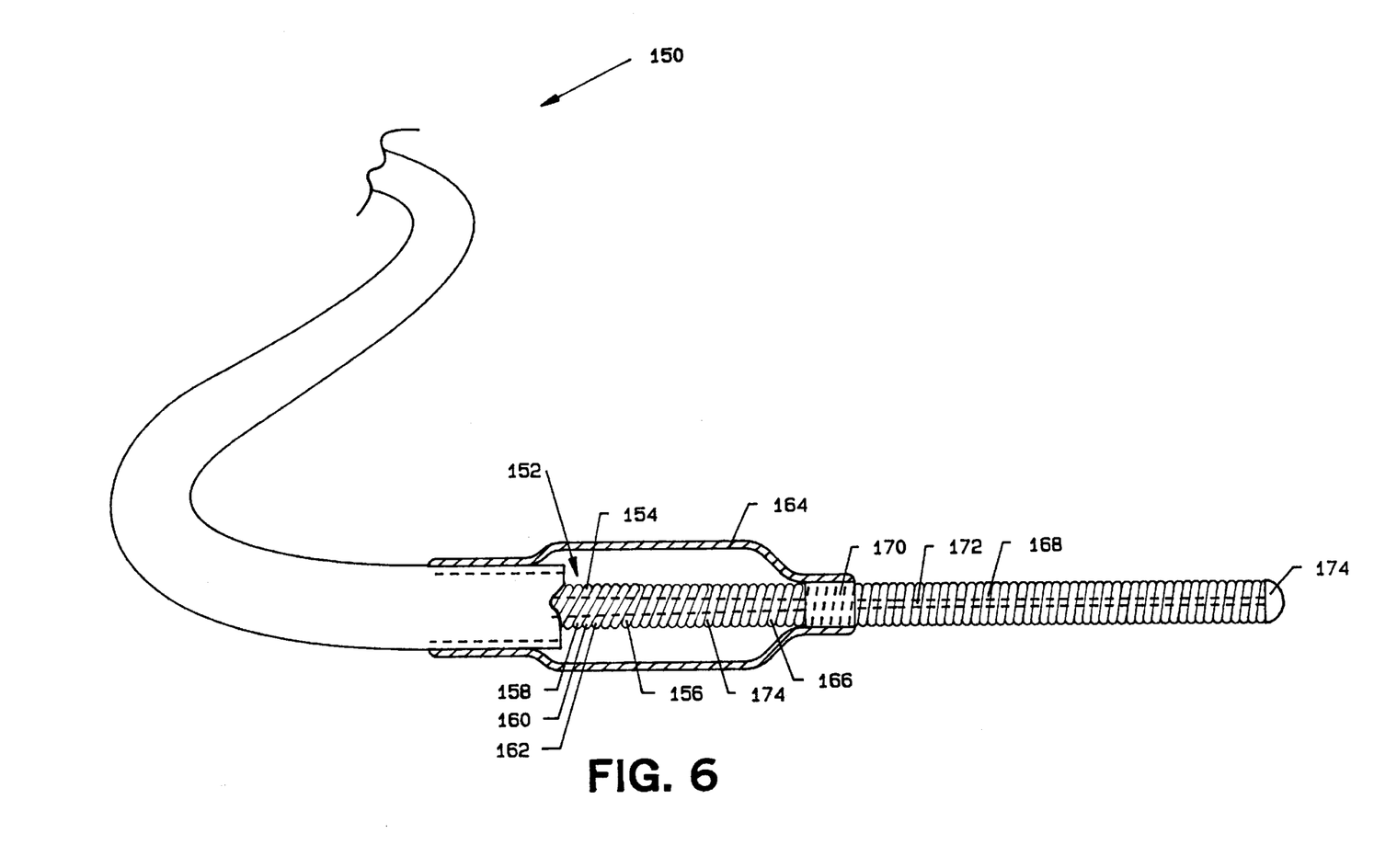
FIG. 6 is a partial cross-sectional view of a fixed-wire balloon catheter utilizing the present invention.

FIG. 6 is a partial cross-sectional view of a fixed-wire balloon catheter 150 utilizing the present invention. In this embodiment, a spring coil 152 is a decreasing filar coil having a single platinum wire strand 154 running substantially the entire length of fixed-wire balloon catheter 150. The stainless steel wire strands 158, 160 and 162 are aligned next to and with the single platinum wire 154 to form the decreasing filar spring coil 152 which is similar to the coil 70 described in FIG. 4. The platinum wire strand 154 undergoes a substantial change in pitch starting at point 156 where the wire strands 158, 160 and 162 are sequentially terminated within the length of a balloon 164 to provide a unifilar coil 166 of equivalent coil spacing to the decreasing filar coil 152. The unifilar coil portion 166 extends into the distal end of the balloon 164. A steerable unifilar coil 168 is secured by a weldment 170 to the unifilar wound marker portion 166 including only the singular radiopaque wire strand 154 and is designed to be more flexible than the main body of fixed-wire balloon catheter 150. Weldment 170 is an air tight seal for inflation of the balloon. A core wire 172 is welded to and extends from the distal tip 174 through the steerable unifilar coil 168, the decreasing filar coil 152, and along the length of the fixed wire balloon catheter 150. The illustrated embodiment is not to be construed as limiting of the present invention as the teachings can be incorporated into similar like structures.

Figure 7:
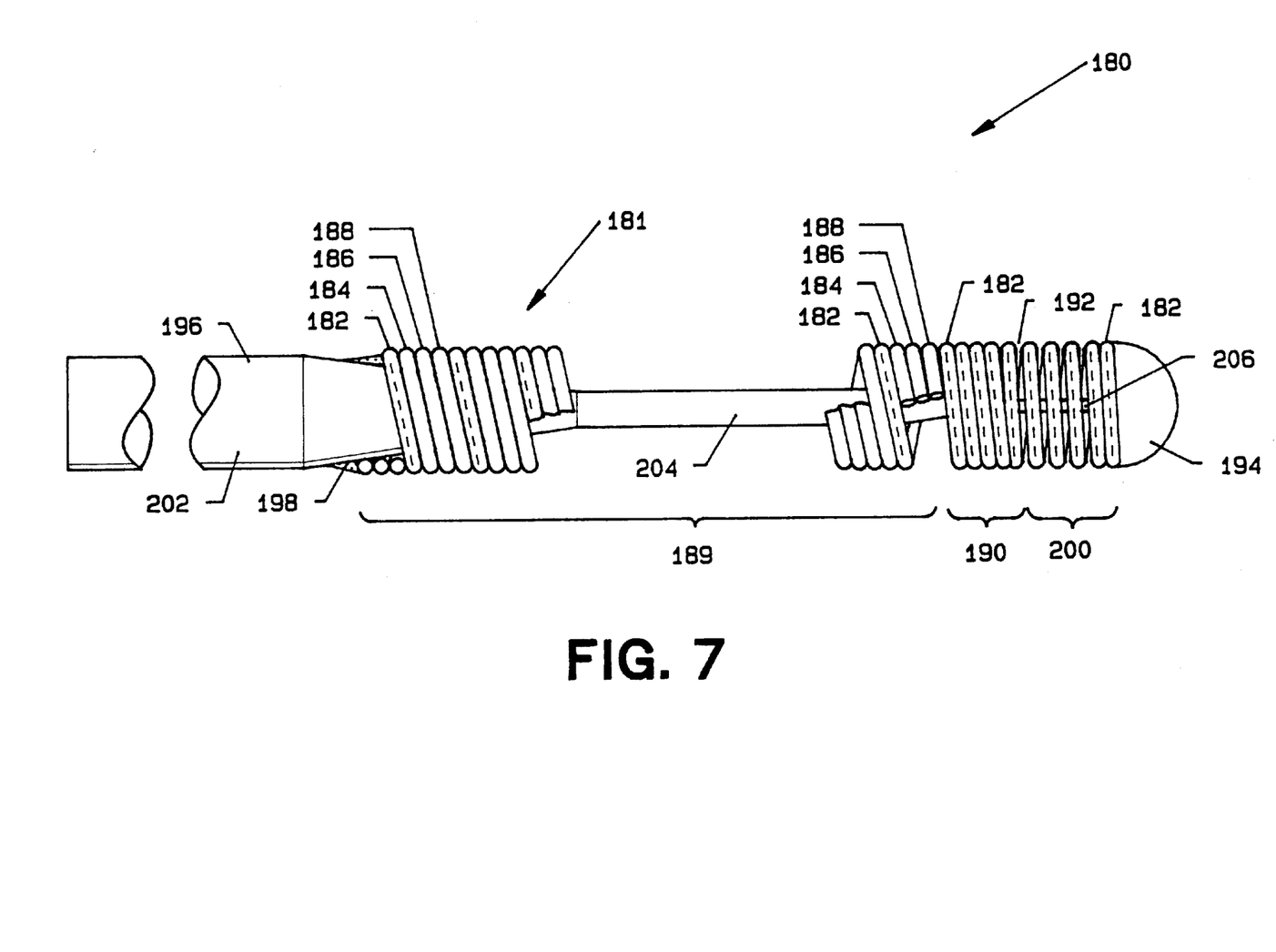
FIG. 7 is a partial cutaway view of a guide wire incorporating a substantially quadrifilar spring coil.

FIG. 7 illustrates a partial cutaway view of a guide wire 180 incorporating a substantially quadrifilar spring coil 181. Wire strands 184, 186 and 188 in the quadrifilar spring coil 181 are drawn from a typical material such as stainless steel. A wire strand 182 adjacent to the wire strands set 184–188, is radiopaque in that it is made of radiopaque material, such as a platinum/irridium alloy. The illustration of the radiopaque wire strand 182 includes a resident dashed line for purposes of illustration. The main body of the coil 181 including wire strands 182–188 are quadrifilar wound along region 189 until nearing the distal end where the wire strand coils 184, 186 and 188 are discontinued, leaving just the radiopaque wire strand 182 which is unifilar and close wound as depicted by region 190. The wires 184, 186 and 182 are suitably terminated and are brazed to each other and to wire 182 forming a suitable termination as illustrated, which optionally could also be a tapered termination. Beginning at point 192, the unifilar radiopaque wire strand 182 is spread and spaced from itself and continues in this mode along region 200 until meeting the distal tip 194 where it is secured such as by welding to the distal tip. The opposing end of the quadrifilar spring coil 181 is secured to the tapered core wire 196 by a weldment 198.

The coil regions 189, 190 and 200 present varying intensity, viewable traces when viewed fluoroscopically. Region 189 presents a relatively faint trace whereas regions 190 and 200 present stronger and sharper more distinct traces. Region 190 is closely wound, and has the strongest and sharpest trace of the regions 190 and 200. Region 200 has a trace level between the levels of those indicated in region 190 and 189 dedicated to the spacing of the coils in the region 200. The spacing of the radiopaque wire 182 can be varied to yield different viewable trace levels as required. The regions 190 and 200 can also be of different longitudinal lengths than those illustrated by way of example and for purposes of illustration only, and are not to be construed as limiting of the present invention.

It is noted that the core wire 196 ramps down from the larger diameter 202 to a intermediate diameter 204, and then to a smaller diameter 206 where each successive smaller diameter area becomes increasingly less rigid. The decreasing core wire diameter along with the spaced unifilar coil winding 182 in region 200 renders the just described area quite flexible so that it may readily and without rigidity follow any tortious path through the human body. The spaces between the unifilar windings in region 200 allows the windings to flex and be as flexible as may be required.

In one example, the PTCA wire with platinum tracer and integral distal spring is designed to provide radiographic visualization throughout the coil length and without potential for poor visualization of balloon marks by providing a tracer wire in the proximal area of spring for subdued visualization so as not to interfere with balloon markers and yet still be able to be seen. The distal area of tracer coil has a decrease in pitch in order to improve or enhance radiographic visualization so as to readily identify guide wire tip position.

The main body of the coil is wound with multiple filars incorporating a tracer strand of platinum alloy and can be more than one strand depending on the amount of radiopacity desired. The remaining strands can be stainless steel. Near the distal end, the other wires are dropped off, but the platinum strand(s) continue in the coil to the distal connection. The pitch of distal segment could be varied from tight wound to space between windings for improved flexibility.

Figure 8:
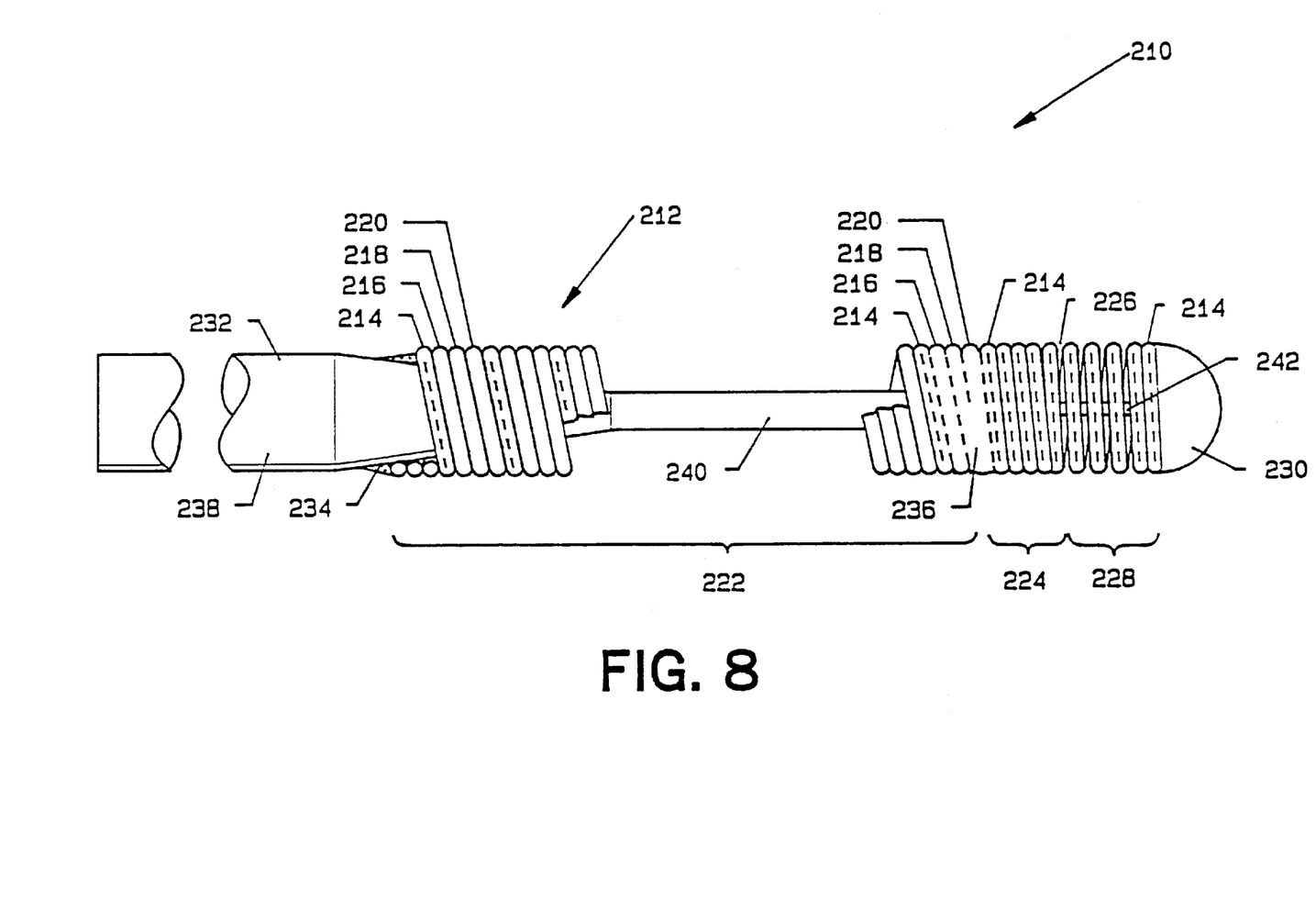
FIG. 8 is a cutaway view of a guide wire incorporating a quadrifilar spring coil; and, FIG. 9 is a partial cross-sectional view of an infusion guide wire employing the present invention.

FIG. 8 is substantially similar to that of FIG. 7 as previously described, and illustrates a cutaway view of a guide wire 210 incorporating a quadrifilar spring coil 212. Wire strands 216, 218 and 220 in the quadrifilar spring coil 212 are drawn from a typical material such as stainless steel. A wire strand 214 adjacent to the wire strands set 216–220, is radiopaque in that it is made of radiopaque material, such as a platinum/irridium alloy. The illustration of the radiopaque wire strand 214 includes a resident dashed line for purposes of illustration. The main body of the coil 212 including wire strands 214–220 are quadrifilar wound along region 222 until nearing the distal end where the wire strand coils 216, 218 and 220 are discontinued leaving just the radiopaque wire strand 214 which is unifilar and close wound as depicted by region 224. Beginning at point 226, the unifilar radiopaque wire strand 214 is spread and spaced from itself and continues in this fashion along region 228 until meeting the distal tip 230 where it is secured such as by welding to the distal tip. The opposing end of the quadrifilar spring coil 212 is secured to the tapered core wire 232 by a weldment area 234. A weldment area 236 secures the coils 214–220 in the distal end of region 222 to the core wire 232.

The coil regions 222, 224, and 228 present varying intensity viewable traces when viewed fluoroscopically. Region 222 presents relatively faint trace whereas regions 224 and 228 present stronger and sharper traces. Region 224 is closely wound and has the strongest and sharpest trace of the regions 222 and 228. Region 228 has a trace level between the levels of those indicated in region 224 and 222 owing to the spacing of the coils in the region 228. The spacing of the radiopaque wire 214 can be varied to yield different trace levels as required. The regions 224 and 228 can also be of different lengths than those illustrated by way of example and for purposes of illustration only and are not to be construed as limiting of the present invention.

It is noted that the core wire 232 ramps down from the larger diameter 238 to a intermediate diameter 240 and then to a smaller diameter 242 where each successive smaller diameter areas becomes increasingly less rigid. The decreasing core wire diameter along with the spaced unifilar coil winding 214 in region 228 renders the area at the just described area quite flexible so that it may readily and without rigidity follow any tortious path. The spaces between the unifilar windings in region 228 allows the windings to flex as required.

Figure 9:
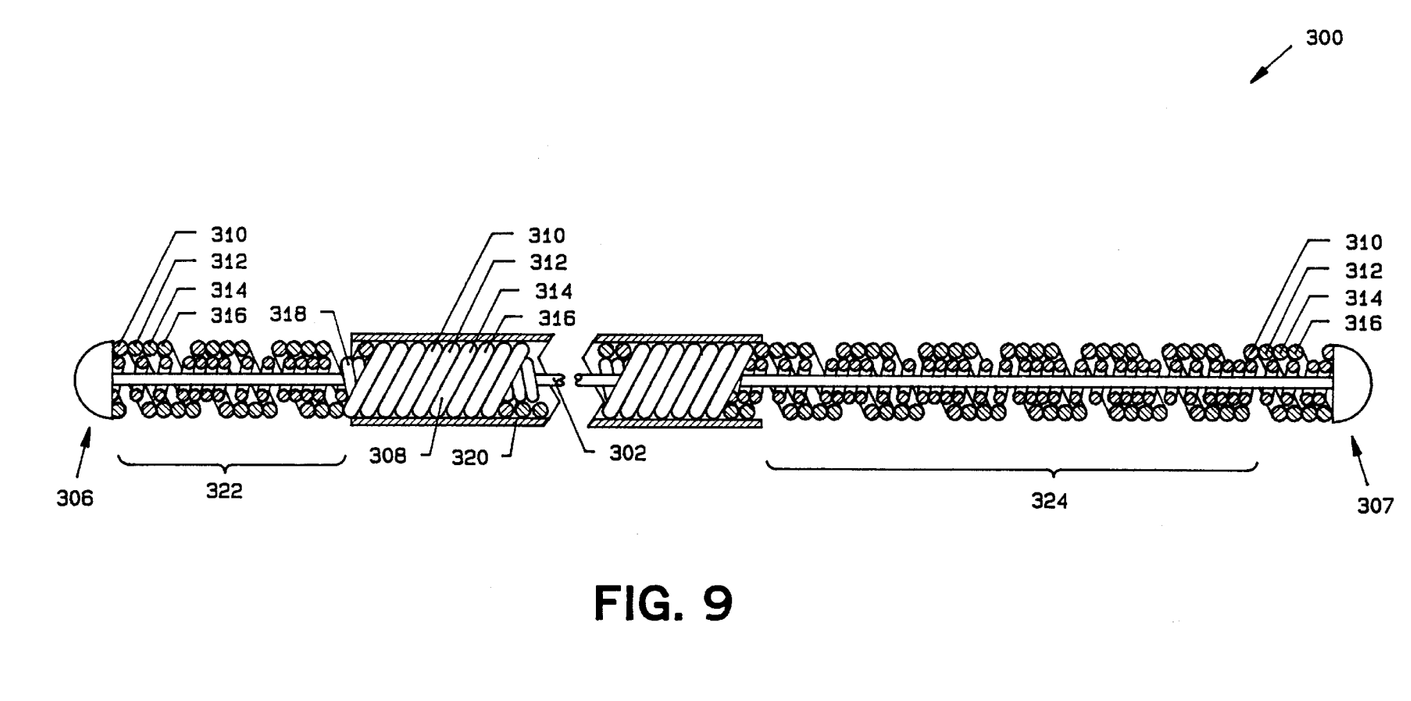

FIG. 9 is a partial cross-sectional view of an infusion guide wire 300 employing the present invention. A solid core wire 302 is within the center and runs the entire length of the infusion guide wire 300. Liquid is infused into the proximal end 306 in the region 322 and dispensed from the distal end 307 in the region 324 of the infusion guide wire 300 through spaces in the turns. The outer coil 308 is of a common quadrifilar construction including four strands of wire. Strand 310 is radiopaque and is of a platinum alloy. Strands 312, 314 and 316 of the outer coil are stainless steel. An inner coil 318 aligns coaxially within the lumen formed by the outer quadrifilar coil 308 and over and about the solid core wire 302. A flexible plastic sheath 320 aligns over and about the outer periphery of the outer quadrifilar coil 308, and extends toward but short of the proximal end in one direction, thus leaving a region 322 of the coaxially aligned inner and outer coils 308 and 318 exposed for the infusion of liquid drugs from a suitable dispensing structure. The flexible plastic sheath 320 extends in the opposite direction toward the distal end 307, but short of the distal end 307 leaving a region 324 of the coaxially aligned outer and inner coils 308 and 318 uncovered so that drugs can be dispensed therefrom. The outer and inner coils 308 and 318 in regions 322 and 324 are spread and spaced so that fluid can flow freely into the region 322, inside of the sheath 320 and along the lumen formed by the inner coil 318 and freely out of the spread coils in region 324. The coils lying beneath and coaxially to the sheath 320 are not spread and are closely wound. Fluid flows between the inner core wire and the lumen of inner coil 318.

Mode of Operation

The main body of wire coil is wound with multiple filars incorporating a tracer strand of platinum alloy. There can be more than one strand depending on the amount of radiopacity desired. The remaining strands can be stainless steel. Near the distal end, the filars are dropped off all but the platinum strands which continue to coil to the distal end. The pitch of the distal end can be varied from tight wound to a space wound between windings for improved flexibility.

The present invention is designed to provide radiographic visualization throughout the coil length, but without potential for poor visualization. The distal area of tracer coil can have a decrease in pitch in order to improve or enhance radiographic visualization so as to readily identify the guide wire tip position.

Having thus described the preferred embodiments of the present invention, those of skill in the art will be able to apply the teachings found herein to yet other embodiments within the scope of the claims hereto attached. The teachings of the present invention can be implemented into medical structures, and any other structures as may be deemed necessary for similar procedures requiring viewing and traceability.

I claim:

1. A guide wire having a multi filar coil with a plurality of separate wire strands, comprising:
   a. at least one of said plurality of separate wire strands drawn of a radiopaque material; and,
   b. at least two other of said plurality of separate wire strands of a non-radiopaque material: said plurality of wire strands being wound together in multifilar fashion such that said guide wire exhibits at least three different intensities of radiopacity along its length.

2. A guide wire according to claim 1 wherein said at least one of said plurality of separate wire strands drawn of said radiopaque material is longer than one of said at least two other of said plurality of separate wire strands of said material.

3. A guide wire according to claim 2 wherein said multifilar coil has a constant winding angle.

4. A guide wire comprising:
   a. a first coil of a radiopaque material having a proximal end and a distal end; and, b. second and third coils of a non-radiopaque alloy material having proximal ends and distal ends wound in multifilar fashion with respect to said first coil such that said guide wire exhibits at least three different intensities of radiopacity along its length.

5. A guide wire according to claim 4 wherein said first coil is longer than said second coil.

6. A guide wire according to claim 5 wherein said proximal end of said first coil is adjacent said proximal end of said second coil.

7. A guide wire according to claim 6 wherein said first coil is wound at a different pitch distal to said distal end of a said second coil.

8. A guide wire according to claim 7 wherein said second coil pitch is of a pitch sufficient to maintain the same coil spacing proximal and distal.

9. A guide wire including a multifilar coil with a plurality of separate wire strands comprising:
   a. at least one of said plurality of separate wire strands drawn of radiopaque material; and,
   b. at least two other of said plurality of separate wire strands of a non-radiopaque alloy wire strand material; said plurality of wire strands being wound together in multifilar fashion such that said guide wire exhibits at least three different intensities of radiopacity along its length.

10. A guide wire with a platinum tracer and an integral distal spring comprising:
    a. main body of coil wound with multiple filars and including at least one tracer strand of a platinum alloy; and,
    b. a distal end including platinum strands of variable spacing or variable pitch and secured to a distal end of said main body; said main body of coil being wound such that said guide wire exhibits at least three different intensities of radiopacity along its length.

11. The guide wire of claim 10 including means terminating said multiple filars before a distal tip.

12. The guide wire of claim 10 including means terminating said multiple filars before a distal tip and means securing said terminating means to said core wire.

13. A guide wire having various degrees of radiopacity, comprising:
    a. a first guide wire portion comprising a strand of radiopaque material and three strands of non-radiopaque material wound in a multifilar fashion;
    b. a second guide wire portion comprising a strand of radiopaque material and two strands of non-radiopaque material wound in a multifilar fashion; and,
    c. a third guide wire portion comprising a strand of radiopaque material and a strand of non-radiopaque material wound in a multifilar fashion.

14. The guide wire of claim 13, further comprising a fourth guide wire portion comprising a strand of radiopaque material.

15. The guide wire of claim 13 having a proximal end and a distal end, wherein said first guide wire portion is at said proximal end, and said second and third guide wire portions are increasingly distal to said proximal end.

16. The guide wire of claim 13 wherein said first guide wire portion exhibits a weaker fluoroscopic trace relative to said second guide wire portion.

17. The guide wire of claim 13 wherein said second guide wire portion exhibits a weaker fluoroscopic trace relative to said third guide wire portion.

18. The guide wire of claim 14, wherein said third guide wire portion exhibits a weaker fluoroscopic trace relative to said fourth guide wire portion.

19. The guide wire of claim 13, wherein said radiopaque material comprises platinum.

20. The guide wire of claim 13, wherein said non-radiopaque material comprises stainless steel.

21. A guide wire having various degrees of radiopacity, comprising
    a. an outer coil comprising:
       a first outer coil portion comprising a strand of radiopaque material and three strands of non-radiopaque material wound in a multifilar fashion;
       a second outer coil portion comprising a strand of radiopaque material and two strands of non-radiopaque material wound in a multifilar fashion; and
       a third outer coil portion comprising a strand of radiopaque material and a strand of non-radiopaque material wound in a multifilar fashion; and
    b. an inner coil around which said outer coil is wound.

22. The guide wire of claim 21, wherein said inner coils is quadrifilar.

23. The guide wire of claim 21, wherein said inner coil comprises at least one strand of radiopaque material.

* * * * *